US010729871B2

(12) United States Patent
Niedermann et al.

(10) Patent No.: US 10,729,871 B2
(45) Date of Patent: Aug. 4, 2020

(54) VAPOR DELIVERY SYSTEM

(71) Applicant: Crane USA Inc., Itasca, IL (US)

(72) Inventors: Dirk Niedermann, Bloomingdale, IL (US); Kin Wan Li, Fanling (HK); Poon Lap Chan, Shatin (HK); James G. Montagnino, St. Charles, IL (US)

(73) Assignee: Crane USA Inc., Itasca, IL (US)

(*) Notice: Subject to any disclaimer, the term of this patent is extended or adjusted under 35 U.S.C. 154(b) by 981 days.

(21) Appl. No.: 15/271,927

(22) Filed: Sep. 21, 2016

(65) Prior Publication Data

US 2018/0078729 A1   Mar. 22, 2018

(51) Int. Cl.
| A61M 16/16 | (2006.01) |
| A61H 33/12 | (2006.01) |
| A61M 16/10 | (2006.01) |
| A61M 16/06 | (2006.01) |
| A61M 11/00 | (2006.01) |
| A61M 11/04 | (2006.01) |
| A61M 16/00 | (2006.01) |

(52) U.S. Cl.
CPC .......... *A61M 16/109* (2014.02); *A61H 33/12* (2013.01); *A61M 11/005* (2013.01); *A61M 11/042* (2014.02); *A61M 16/022* (2017.08); *A61M 16/06* (2013.01); *A61M 16/16* (2013.01)

(58) Field of Classification Search
CPC ..... A61H 33/12; A61M 16/16; A61M 16/109; A61M 16/18; A61M 16/06; A61M 11/042
See application file for complete search history.

(56) References Cited

U.S. PATENT DOCUMENTS

| 3,152,240 | A | * | 10/1964 | Scott | A61H 33/12 392/403 |
| 3,351,737 | A | * | 11/1967 | Katzman | A61H 33/12 392/337 |
| 4,621,641 | A | * | 11/1986 | Frank | A61H 33/12 392/404 |
| 4,903,850 | A | * | 2/1990 | Frank | A61M 16/16 392/403 |
| 6,101,317 | A | * | 8/2000 | Stern | A61H 33/12 219/222 |
| 2004/0025242 | A1 | * | 2/2004 | Leung | A61H 33/12 4/524 |
| 2006/0283405 | A1 | * | 12/2006 | Chou | A61H 33/063 122/32 |
| 2017/0020781 | A1 | * | 1/2017 | Tang | A61H 33/12 |

\* cited by examiner

*Primary Examiner* — Bradley H Philips
(74) *Attorney, Agent, or Firm* — Wood, Phillips, Katz, Clark & Mortimer

(57) ABSTRACT

A vapor delivery system having: a) a base unit configured to generate a supply of vapor; and b) a vapor control system configured to allow a user to selectively: a) cause vapor generated by the base unit to be discharged primarily to a surrounding space within which the base unit resides to thereby increase vapor density in the surrounding space; and b) cause vapor generated by the base unit to be discharged primarily to a vapor guide structure configured to: i) be placed operatively with respect to a user's face; and ii) guide discharging vapor generated by the base unit into at least one of the user's nose and mouth with the vapor guide structure placed operatively with respect to the user's face.

17 Claims, 7 Drawing Sheets

VAPOR DELIVERY SYSTEM

BACKGROUND OF THE INVENTION

Field of the Invention

This invention relates to an apparatus for generating vapor and, more particularly, to an apparatus that can be used selectively as: a) an environmental humidifier; and b) a personal inhaler.

Background Art

Many portable apparatus are currently available for increasing vapor density in air to promote better breathing. Different structures are used to generate vapor, among which are those utilizing ultrasonic vibration and those using a heat source. The former causes small liquid droplets to be entrained in the air, with the latter generating vapor emanating from the heat source. Throughout the disclosure herein, including the claims, "vapor" will be used to generically identify any form of a fluid that is entrained in environmental air to increase the fluid density in the air.

Heretofore, the industry has maintained two different categories for vapor generating products—room humidifiers and personal inhalers. Room humidifiers generally use a refillable reservoir that feeds water to a vapor generating structure. Generated vapor is caused to be discharged continuously in a stream that expands upon discharge to disperse in the surrounding environment. These devices may rely upon nothing more than the light vapor's tendency to rise to distribute in a space. Alternatively, structure may be provided to induce flow of the vapor that causes dispersion into a larger air volume.

Inhalers are typically designed with a mask that can be placed conformingly against a user's face to create a chamber around the mouth and nose. A discrete amount of liquid is heated to generate vapor which a user can inhale from the mask chamber. These devices are typically designed to create a relatively stagnant vapor mass in the chamber that is drawn into a user's nose and mouth as the user inhales.

While the above two categories of products may both utilize the same type of vapor, they operate differently in the respect that one is designed to discharge vapor into a large volume of air whereas the other is designed simply to create a low pressure vapor mass that can be comfortably inhaled by a user. Thus, these categories of products have remained separate in the market. A consumer having respiratory problems, or simply desiring the benefits of both a personal humidifier and inhaler, is forced to purchase and maintain two different products. Given the ever-increasing number of personal care products, the need to purchase and store multiple products is an unwanted expense and a user inconvenience.

Those offering room humidifiers and inhalers must also address safety issues. If vapor is generated by a heat source, care must be taken to reduce the likelihood that a user will inadvertently contact a heated surface during operation. Heated steam may also damage operating parts if it is not properly controlled between steam generation and discharge locations.

Contact with heated surfaces is particularly a concern when a heated surface is directly exposed, as when there is no, or a minimal depth of, water over the heated surface. Aside from safety concerns, allowing an apparatus to completely deplete the water supply may cause the progressive buildup of calcium on a heated surface directly exposed to the water it vaporizes. This condition may compromise performance, necessitate regular cleaning and other maintenance, and may shorten the life span of an apparatus.

The industry continues to seek personal care products for consumers that are affordable, effective, and add to overall user experience.

SUMMARY OF THE INVENTION

In one form, the invention is directed to a vapor delivery system having: a) a base unit configured to generate a supply of vapor; and b) a vapor control system. The vapor control system is configured to allow a user to selectively: a) cause vapor generated by the base unit to be discharged primarily to a surrounding space within which the base unit resides to thereby increase vapor density in the surrounding space; and b) cause vapor generated by the base unit to be discharged primarily to a vapor guide structure. The vapor guide structure is further configured to: i) be placed operatively with respect to a user's face; and ii) guide discharging vapor generated by the base unit into at least one of the user's nose and mouth with the vapor guide structure placed operatively with respect to the user's face.

In one form, the vapor guide structure has a mask housing that is configured to: a) conform at least nominally to the user's face with the vapor guide structure placed operatively with respect to the user's face; and b) define a chamber over the at least one of the user's nose and mouth configured to guide discharged vapor generated by the base unit into the at least one of the user's nose and mouth with the vapor guide structure placed operatively with respect to the user's face.

In one form, the vapor delivery system has first and second different states. With the vapor delivery system in the first state, vapor generated by the base unit is discharged primarily to the surrounding space. With the vapor delivery system in the second state, vapor generated by the base unit is discharged primarily to the vapor guide structure.

In one form, the vapor control system has a first subassembly and a second subassembly. The first and second subassemblies are interchangeably operatively connected to the base unit to respectively place the delivery system in the first and second states.

In one form, the first subassembly has a housing defining a reservoir for a supply of liquid to be delivered to the base unit.

In one form, the base unit has a receptacle for a supply of liquid to be vaporized by the vapor delivery system.

In one form, the first subassembly has a housing defining a reservoir for a supply of liquid. The reservoir is in fluid communication with the receptacle with the delivery system in the first state.

In one form, the base unit has a receptacle for a supply of liquid to be vaporized by the vapor delivery system. The receptacle is in fluid communication with the chamber with the delivery system in the second state.

In one form, the second subassembly is configured to allow a user to selectively control a rate of vapor delivery from the base unit to the mask housing chamber.

In one form, the mask housing has at least one vent opening through which fluid can discharge from the mask housing chamber to the surrounding space with the vapor guide structure placed operatively with respect to the user's face.

In one form, the second subassembly has an adaptor that is configured to be supported on the base unit with the vapor delivery system in the second state. The second subassembly further includes a first unit that is releasably connected to the adaptor and defines the mask housing.

In one form, the first unit is made from a formed flexible material.

In one form, the first subassembly has an adaptor that is configured to be supported on the base assembly with the vapor delivery system in the first state.

In one form, the base unit has a receptacle for a supply of liquid to be vaporized by the vapor delivery system. The adaptor is configured to be separated from the housing.

In one form, the adaptor has an upwardly converging surface around a vapor passage/space that guides upward vapor flow from the base unit.

In one form, the reservoir has a vertical depth. The upwardly converging surface extends over at least a part of the vertical depth of the reservoir.

In one form, the housing defines a downwardly converging collection surface that is configured to funnel liquid downwardly into the vapor passage.

In one form, the downwardly converging collection surface extends over at least a part of the vertical depth of the reservoir.

In one form, the base unit and adaptor are configured to cause environmental air and vapor generated by the base unit to be mixed in a space bounded by a surface on the adaptor.

In one form, the base unit has a receptacle for a supply of liquid. The adaptor is configured to vertically overlie a portion of the receptacle.

DETAILED DESCRIPTION OF THE PREFERRED EMBODIMENT

Figures 1, 2, 3, 4:
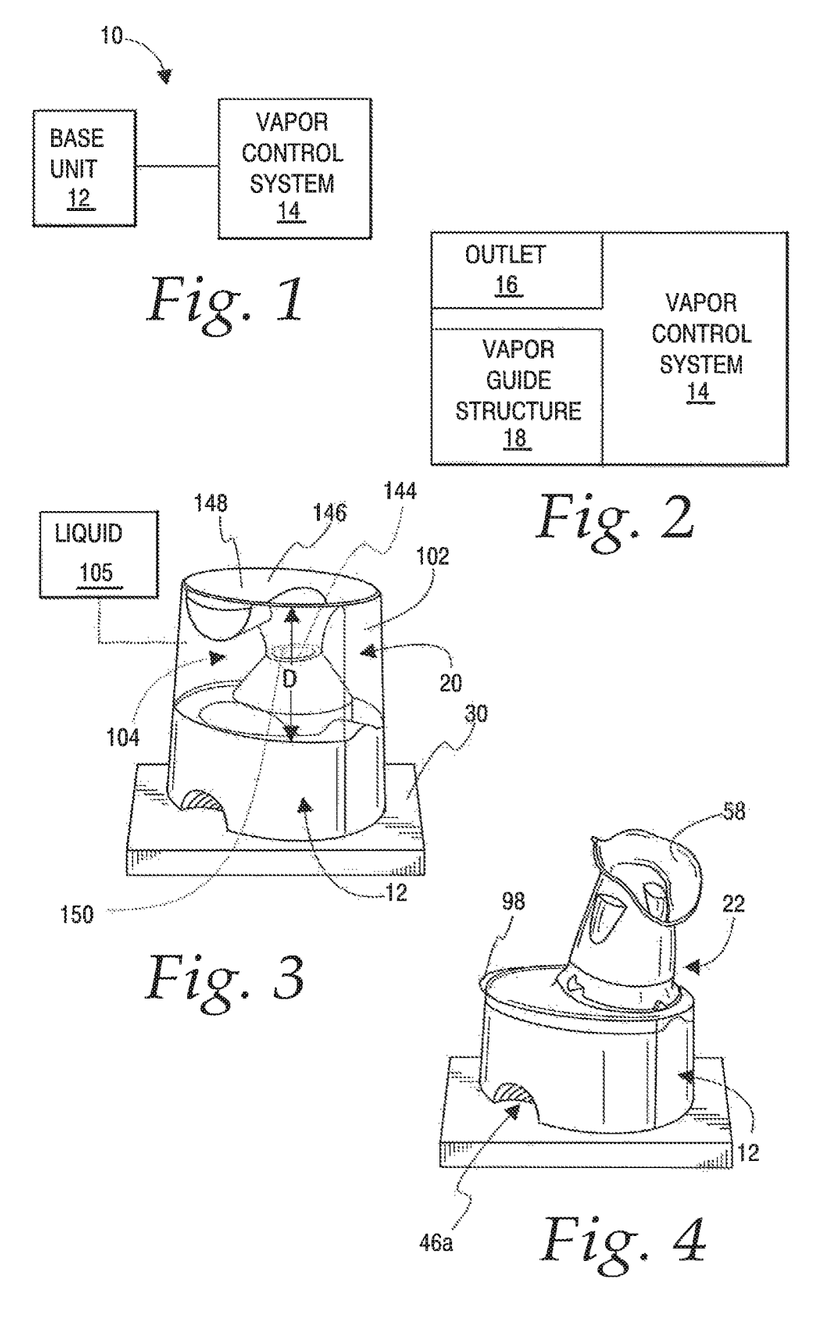
FIG. 1 is a schematic representation of a vapor delivery system, according to the present invention, and consisting of a base unit and a vapor control system.
FIG. 2 is a schematic representation of one specific form of the vapor control system that can be reconfigured to change a state of the vapor delivery system.
FIG. 3 is a perspective view of one specific form of vapor delivery system in a first state wherein a first subassembly is operatively connected to the base unit.
FIG. 4 is a view as in FIG. 3 with the vapor delivery system in a second state wherein a second subassembly is operatively connected to the base unit.

In FIG. 1, a vapor delivery system, according to the present invention, is shown schematically at 10. The vapor delivery system 10 consists of a base unit 12 configured to generate a supply of vapor. A vapor control system at 14 is configured to allow a user to selectively: a) cause vapor generated by the base unit 12 to be discharged primarily to a surrounding space within which the base unit 12 resides to thereby increase vapor density in the surrounding space; and b) cause vapor generated by the base unit 12 to be discharged in a controlled fashion to be inhaled by a user through at least one of his/her nose and mouth.

The schematic representation of the vapor delivery system 10 is intended to encompass virtually an unlimited number of structures that can be changed between different states by a user so that the user can selectively cause the vapor to: a) treat a surrounding space; and b) be generated in a manner whereby it can be conveniently inhaled by the user through his/her nose and/or mouth. The schematic showing is intended to encompass designs wherein simple repositioning of parts might change the state of the vapor delivery system. Alternatively, parts may be interchanged to effect this change in state. The generic showing of the vapor delivery system 10 is intended to encompass all such structures, with the specific form described hereinbelow only exemplary in nature.

In one exemplary form for the vapor control system 14, as shown schematically in FIG. 2, with the vapor control system 14 in a first state, generated vapor discharges to the surrounding space through an outlet 16. With the vapor control system 14 in a second state, generated vapor is discharged primarily to a vapor guide structure 18 that is configured to: a) be placed operatively with respect to a user's face; and b) guide discharging vapor generated by the base unit 12 into at least one of the user's nose and mouth with the vapor guide structure 18 placed operatively with respect to the user's face.

The vapor guide structure 18 might take a number of different configurations that allow a user to strategically situate his/her face, whereby inhalation of vapor generated by the base unit 12 can be conveniently and comfortably carried out.

One specific form of the invention will now be described with respect to FIGS. 3-15. As noted above, this embodiment is exemplary in nature only and should not be viewed as limiting with respect to any of the specific components or their interaction.

The vapor delivery system 10 consists of a first subassembly 20 and a second subassembly 22 that are interchangeably operatively connected to the base unit 12. With the first subassembly 20 operatively connected to the base unit 12, as shown in FIG. 3, the vapor delivery system 10 is in its first state. With the second subassembly 22 operatively connected to the base unit 12, as shown in FIG. 4, the vapor delivery system 10 is in its second state.

The base unit 12 has a housing 24 that contains the basic operating components 26. Basic operation of the base unit 12 will be described without a detailed description of the components 26. The basic technology for generating vapor is well known in this industry and it is contemplated that any existing technologies may be used to generate vapor and allow a user to input controls for desired operating characteristics.

The housing 24 is configured so that a downwardly facing region 28 can be placed against a subjacent surface 30 to support the base unit in an operative orientation.

The housing 24 defines a top wall 32 that extends around a receptacle 34. The receptacle 34 is configured to retain a supply of liquid, typically water, to be vaporized by the vapor delivery system 10. In this embodiment, the receptacle 34 is bounded by a peripheral wall 36 and a bottom wall 37. The peripheral wall 36 has an overall shape of the number "8", as viewed in plan, whereby there are larger and smaller sub-receptacles 38, 40, respectively, in open communication with each other and together defining the receptacle 34.

The peripheral wall 36 is stepped to define a continuous, upwardly facing ledge 42 provided primarily to allow a user to readily visibly gauge the optimal amount of liquid to be placed in the receptacle 34 for use with the vapor delivery system 10 in its second state.

The top wall 32 has spaced vents 44a, 44b therethrough to allow vertical passage of fluid drawn in from the atmosphere through housing vents 46a, 46b, respectively. The vents 46a, 46b are located where there are voids in the periphery of the housing 24 so that they will remain fully exposed, and not prone to being blocked, as by a plush supporting surface 30, with the base unit 12 operatively supported on that surface 30.

As noted above, the precise structure for generating the vapor in the vapor delivery system 10 is not critical to the present invention. The vapor may be generated ultrasonically, as through a structure disclosed in U.S. Pat. No. 8,308,145, the disclosure of which is incorporated herein by reference. Alternatively, and more preferably for purposes of the inhaling function, the vapor may be generated by a heater 26a. The bottom of the larger sub-receptacle 38 is bounded by a conductive metal plate 48. The temperature of the plate 48 is elevated through a heat generator 26b. Generated vapor rises from the receptacle 34, primarily directly from over the heated plate 48 in the larger sub-receptacle 38.

When a user desires to use the vapor delivery system in its second state, the second subassembly 22 is placed operatively upon the base unit 12. In this embodiment, the second subassembly 22 is made up of an adaptor 50 and a first unit 52 releasably attached to the adaptor 50. The first unit 52 and adaptor 50 may be made as one piece whereby the entire second subassembly 22 may be considered to be the first unit 52 or adaptor 50, for purposes herein.

Figure 6:
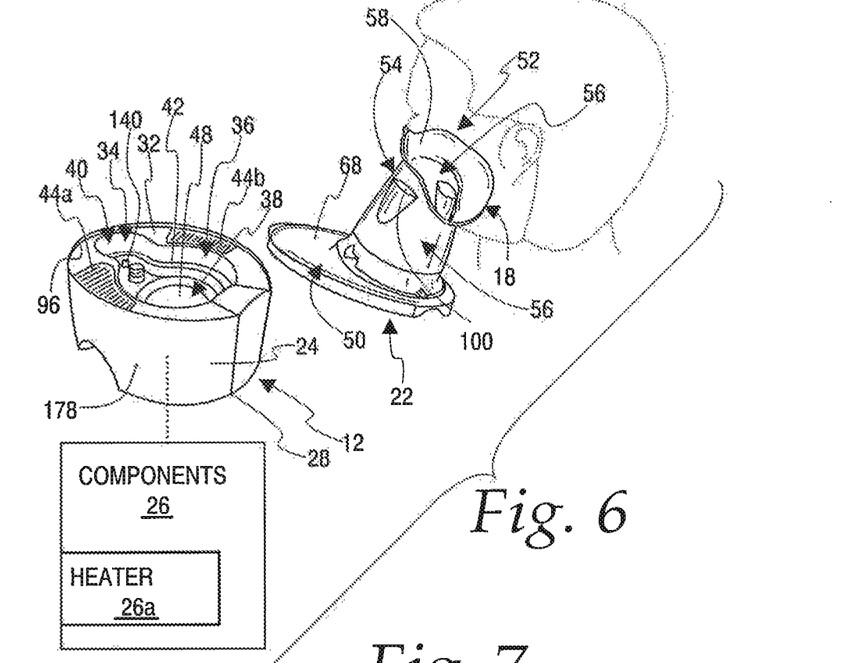
FIG. 6 is an exploded perspective view of the base unit and second subassembly.
Figure 12:
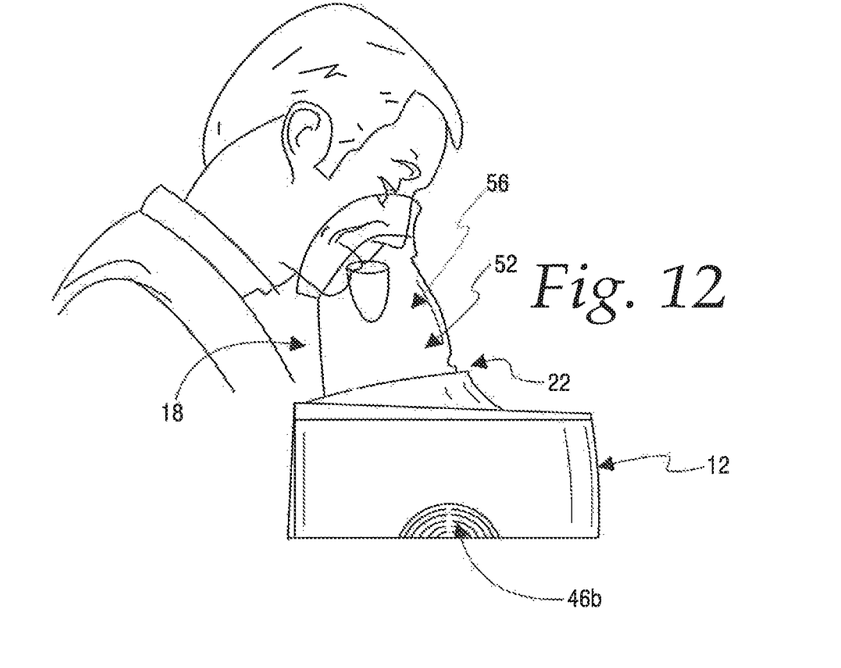
FIG. 12 is a side elevation view of the vapor delivery system in its second state and with a vapor guide structure placed operatively with respect to a user's face.
Figure 13:
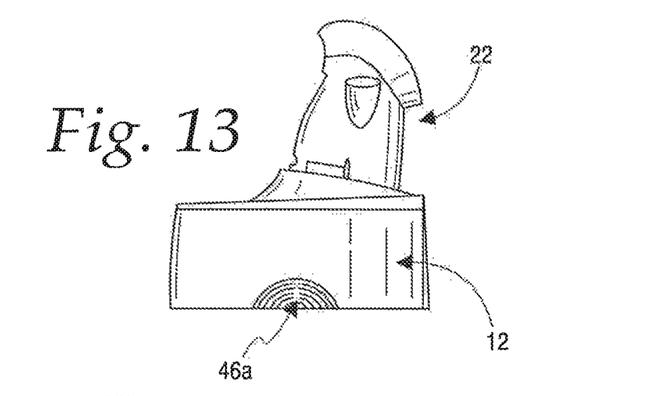
FIG. 13 is a view as in FIG. 12 from the opposite side.
Figure 14:
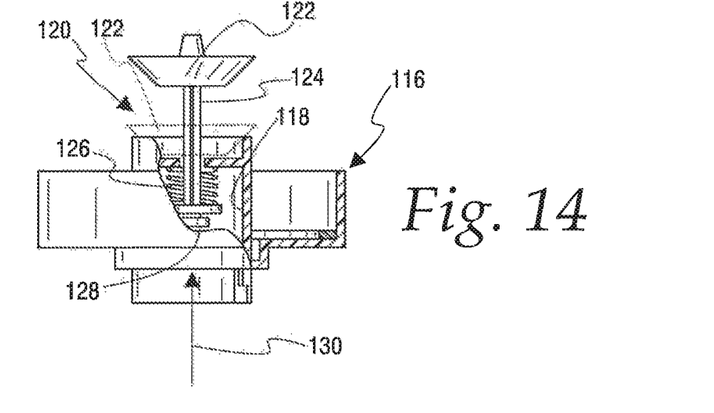
FIG. 14 is an enlarged, partially broken away, view of a cap for an opening to a reservoir on a housing on the first subassembly.

The first unit 52 has a mask housing 54 that makes up part of the vapor guide structure 18 and is configured to: a) conform at least nominally to the user's face with the vapor guide structure operatively placed against the user's face, as shown in FIGS. 6 and 12; and b) define a chamber 56 over at least one of the user's nose and mouth configured to guide discharged vapor generated by the base unit 12 into at least one of the user's nose and mouth with the vapor guide structure 18 placed operatively with respect to the user's face. The mask housing 54 generally has a conventional-type shape, similar to inhaling structures that are used for medical or other purposes. Preferably, all of the first unit 52, or at least a face-engaging rim 58 thereon, is made from a formed flexible material to allow at least nominal conformance to the user's facial region around the nose and mouth area without requiring the application of an uncomfortable amount of pressure. This avoids significant escape of the vapor around the mask housing 54. It should be noted that operative placement of the mask housing 54 is not limited to an arrangement where there is direct contact with the user as depicted.

As depicted, the entire first unit 52 is made from the flexible material and defines a lower region in the form of a sleeve 60 with a surface 62 that frictionally surrounds a rim 64 on a cap 65 on the adaptor 50 to maintain the first unit 52 releasably connected thereto. This connection can be effected through a simple press-fit step.

The adaptor 50 has a depending rim 66 that conforms to and nests against the peripheral wall 36 on the base unit 12 with the second subassembly 22 connected thereto. A top wall 68 on the adaptor 50 and the rim 66 together effectively block the receptacle 34. The user fills the receptacle 34 up to the ledge 42, whereby the remainder of the height of the receptacle 34 defines an available volume for generated vapor. This volume is increased slightly by an upwardly projecting base 70 atop which the cap 65 is located. In this case, the cap 65 is a separate component attached to the top wall 68 though this is not a requirement.

A top wall 72 on the cap 65 has a series of, and in this case three, discrete openings 74a, 74b, 74c through which vapor can pass from the receptacle 34 into the chamber 56.

Figure 9:
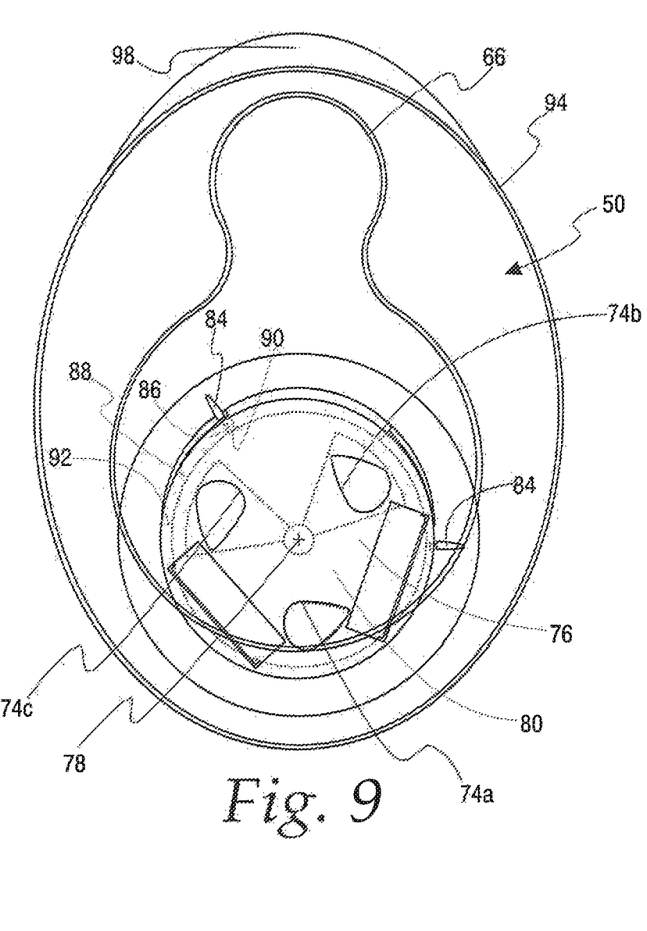
FIG. 9 is a view as in FIG. 8 wherein the control plate is repositioned to change the vapor flow characteristics.
Figure 10:
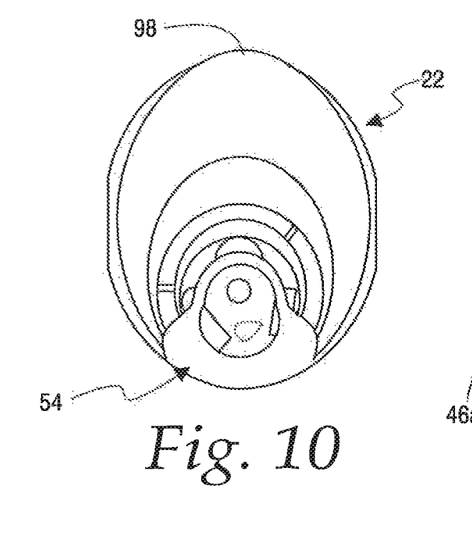
FIG. 10 is a plan view of the second subassembly in FIGS. 4-9.
Figure 11:
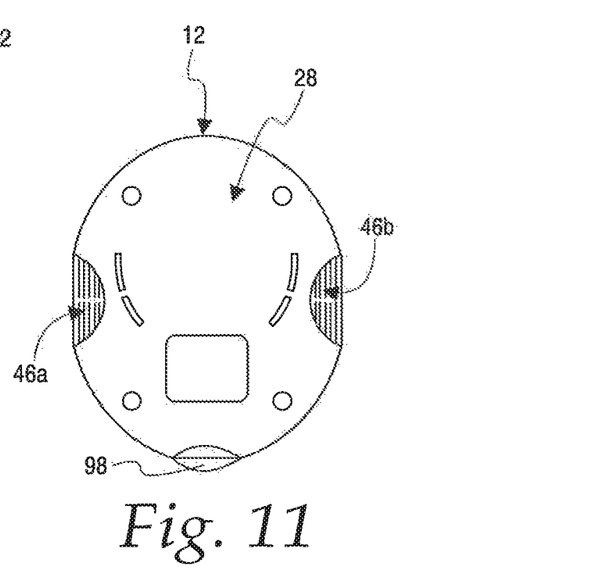
FIG. 11 is a bottom view of the base unit.

A control plate 76 is mounted captively between the cap 65 and base 70 for movement relative to the base 70 around an axis 78. The control plate 76 has a blocking wall 80 through which openings 82a, 82b, 82c are defined. By turning the control plate 76 around the axis 78, the user can select a maximum vapor flow rate state, wherein the openings 82 overlie the openings 74 in full registration, as shown in FIG. 9. Turning the control plate 76 to the FIG. 8 position results in a minimum vapor flow rate with the openings 82, 74 in registration over a lesser area. Different vapor flow rate states can be selected by changing the control plate 76 into different positions between those in FIGS. 8 and 9.

Tabs 84, of like construction, are provided on the control plate 76 at circumferentially spaced locations to allow the user to conveniently turn the control plate 76 around the axis 78 to select the desired flow characteristics. The tabs 84 have associated arms 86 which move in slots 88 bounded by edges 90, 92 that abut each arm 86 to allow consistent user setting of maximum and minimum vapor flow rates.

The base 70 is configured so that the first unit 52 angles from vertical, as seen most clearly in FIG. 12, whereby a user can more conveniently and comfortably place his/her facial region against the rim 58 with the vapor guide structure 18 operatively placed with respect to the user's face.

The adaptor 50 has a depending rim 94 that nests within a complementarily-shaped upwardly projecting rim 96 on the base unit 12. This arrangement allows a simple press fit connection between the adaptor 50 and base unit 12 and facilitates consistent alignment of the adaptor 50 with the base unit 12. A projecting lifting tab 98 facilitates lifting of the adaptor 50 off of the base unit 12 when it is desired to change the state of the vapor delivery system 10.

At least one vent opening 100, and as depicted a plurality of vent openings 100, are provided on the first unit 52 to break vacuum by allowing fluid escape from the chamber 56 as a user is inhaling vapor with the vapor delivery system 10 in its second state.

Figure 15:
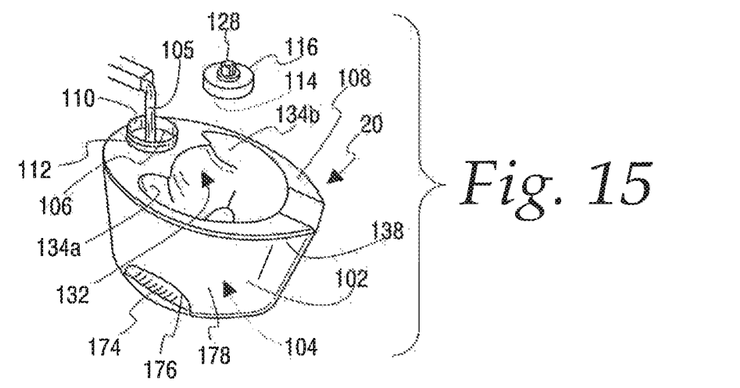
FIG. 15 is a bottom perspective view of the housing defining the reservoir on the first subassembly and showing fluid being introduced to the reservoir.

In one form of the first subassembly 20, as seen in FIGS. 3, 5, 14, and 15, a housing 102 defines a reservoir 104 for a supply of liquid 105 to be delivered to the base unit 12 with the vapor delivery system 10 in its first state. With the housing 102 inverted, as shown in FIG. 15, a fill opening 106 at a bottom wall 108 is accessible. The fill opening 106 is surrounded by a rim 110 with external threads 112 to engage internal threads 114 on a cap 116.

The cap 116 defines an internal through passage 118 for liquid. The passage 118 is controllably blocked by a spring-biased closure assembly 120. The closure assembly 120 includes a blocking part 122 on a stem 124 that is guided for translational movement and biased by a spring 126 into the dotted line position in FIG. 14, wherein the blocking part 122 blocks the passage 118. By exerting a force at the stem end 128 in the direction of the arrow 130, the force in spring 126 is overcome to allow changing of the blocking part 122 from its dotted line position to its solid line position in FIG. 11, whereupon fluid can flow through the passage 118.

A generally cup-shaped surface 132 opens downwardly above the bottom housing wall 108. The surface 132 overlies the larger sub-receptacle 38 on the base unit 12, and defines like guide portions 134a, 134b that situate, one each, over the vents 44a, 44b with the vapor delivery system 10 in the first state.

With the housing 102 inverted as in FIG. 15, and liquid 105 introduced as shown, the reservoir 104 can be filled and thereafter sealed by the cap 116. The housing 102 can then be turned right side up and placed operatively against the base unit 12, as shown in FIG. 3. The bottom of the housing 102, which functions as an adaptor to mate the housing 102 with the base unit 12, has a peripheral edge 138 that seats against the base unit rim 96 to consistently align the housing 102 with the base unit 12.

With the housing 102 placed on the base unit 12, the cap 106 resides in the small sub-receptacle 40. An upwardly projecting post 140 on the base unit 12 engages and progressively elevates the stem 124 as the housing 102 is lowered into place, thereby changing the state of the closure assembly 120 to allow liquid to communicate from the reservoir 104 into the receptacle 34, wherein it can be treated/processed to produce vapor.

The housing surface 132 converges upwardly and defines part of a vapor passage 142 within which vapor flow is guided upwardly from the base unit 12. As seen in FIG. 3, the reservoir 104 has a vertical depth D. The upwardly converging surface 132 extends over at least a part of the vertical depth of the reservoir 104. The surface 132 terminates at an upper opening 144.

The housing 102 has an upper wall 146 with a downwardly converging collection surface 148 that funnels any vapor that may have re-liquefied downwardly into the vapor passage 142 for reintroduction into the liquid receptacle 34. The collection surface 148 has a bottom opening 150 that matches to the opening 144. The resulting structure has essentially an hourglass shape through the reservoir 104 between the top and bottom of the housing 102. As seen, the collection surface 148 extends over at least a part of the depth D of the reservoir 104.

While the first subassembly 20 might be constructed so that vapor generated impinges directly upon the housing surface 132, an additional adaptor 152 is preferably utilized, as part of the first subassembly 20, to change the vapor to a state wherein it is less likely to damage any part of the housing 102. The adaptor 152 consists of a vapor guide portion 154 and a base 156. The base 156 has separate sections 158, 160, that respectively press fit into, and nest within the larger and smaller sub-receptacles 38, 40. With the adaptor 152 operatively pressed into place, an annular ring 162, at the transition between the vapor guide portion 154 and base portion 156, situates above the top wall 32 of the base unit 12. The ring 162 has a plurality of circumferentially spaced, vertically extending slots 164 that admit vapor to a space 166 bounded by a guide surface 168 on the vapor guide portion 154. The vapor guide portion 154 has a truncated conical shape with the vapor guide surface 168 converging upwardly to an outlet at 170 that is located approximately at the location where the openings 144, 150 meet. The outlet 170 has a generally elliptical shape. The vapor outlet 16 for the apparatus 10 is defined in the vicinity of the outlet 170 and openings 144, 150 with the vapor guided in a dispersion pattern by the surface 148.

With this arrangement, the adaptor 152 insulates primarily the housing surface 132 from direct contact by high temperature vapor and additionally is configured so that mixing of vapor and environmental air can occur within the space 166. More specifically, the upward movement of vapor during operation of the system 10 causes atmospheric air to be drawn through the vents 46a, 46b and funneled respectively by walls 172, 172b to and through the vents 44a, 44b in the top wall 32. This incoming air is in turn funneled by the guide portions 134a, 134b to migrate through the slots 164 into the space 166 to mix with the generating vapor. The environmental air effects a slight cooling of the vapor adequate to prevent damage to particularly surfaces of the housing 102 that are in contact with the vapor.

To facilitate handling of the housing 102, spaced grips 174 are formed in recesses 176 through the housing peripheral wall 178 at spaced locations.

A control panel at 180 allows for user inputs, as to allow the user to selectively turn the system on and off, change the amount or rate of vapor generation, etc.

Figure 5:
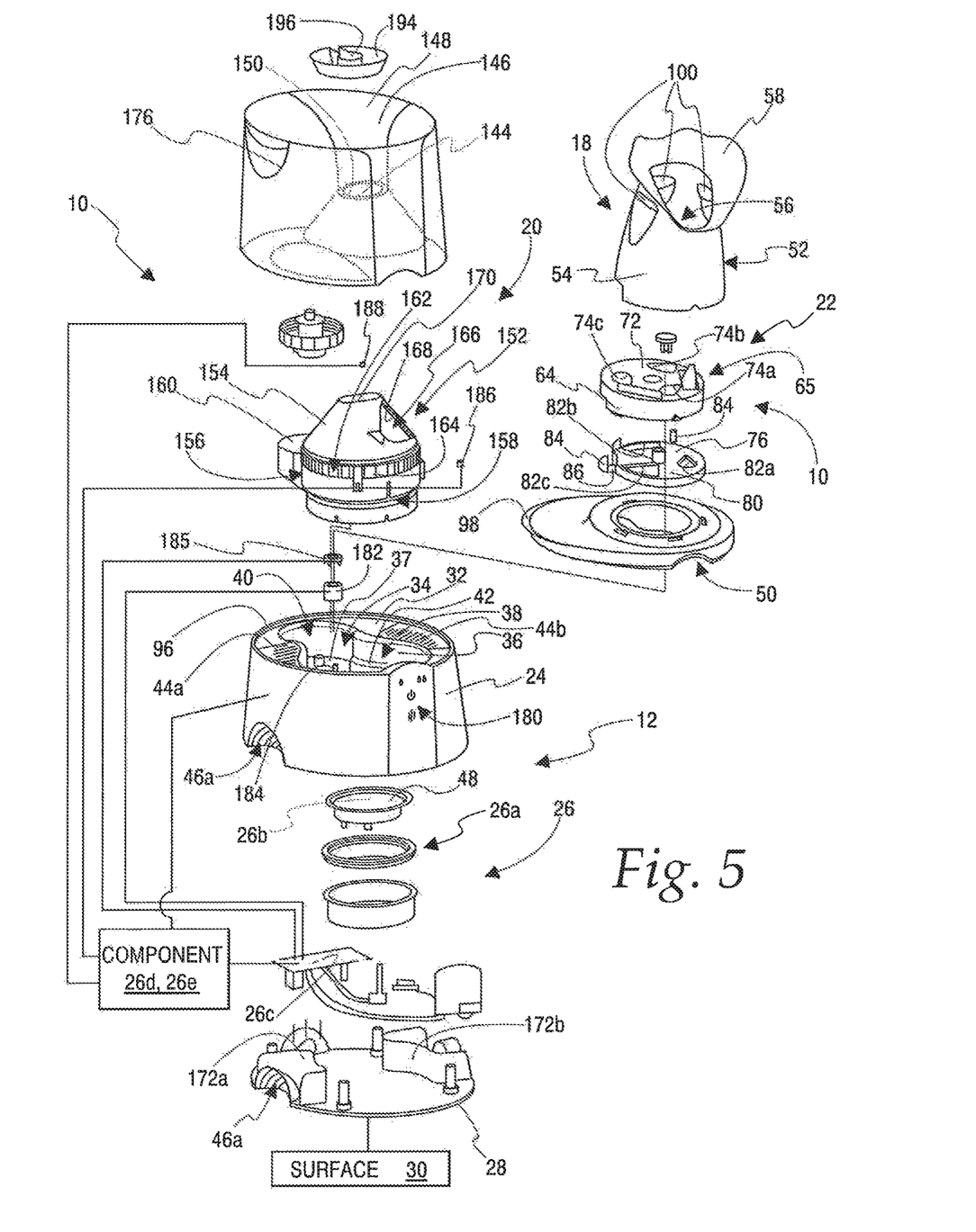
FIG. 5 is an enlarged, exploded, perspective view showing the base unit and the first and second subassemblies in FIGS. 3 and 4.

In addition to allowing manual operation of the system by a user, certain functioning of the system 10 is automatically controlled. These automatic controls, however, are optional. As seen in FIG. 5, an annular buoy 182 floats guidingly vertically upon a post 184 in the receptacle 34. The buoy 182 interacts with an inductor cover 185, with both the buoy 182 and inductor cover 185 electrically connected to a control system 26c. With fluid at a predetermined level within the receptacle 34, the buoy 182 maintains contact with the inductor cover 185 to allow the system to be operated. When fluid level falls below the predetermined amount, the buoy 182 disengages from the inductor cover 185 and the control system 26c causes the system 10 to shut down.

A similar disabling function is afforded by providing separate conductors/magnets 186, 188 on the adaptor 152 and housing 102. The conductors/magnets 186, 188 interact with components 26d, 26e to complete a circuit that causes the control system 26c to enable operation of the system 10. The system 10 may be constructed so that with the adaptor 152 removed, the circuit is interrupted, thereby prohibiting system operation. Similarly, separation of the housing 102 from the base unit 12 may disable the system 10. The system 10 may be designed so that both the adaptor 152 and housing 102 must be operatively positioned to operate the system 10. Alternatively, the system 10 may be operable with either one of the adaptor 152 and housing 102 operatively positioned.

Figure 7:
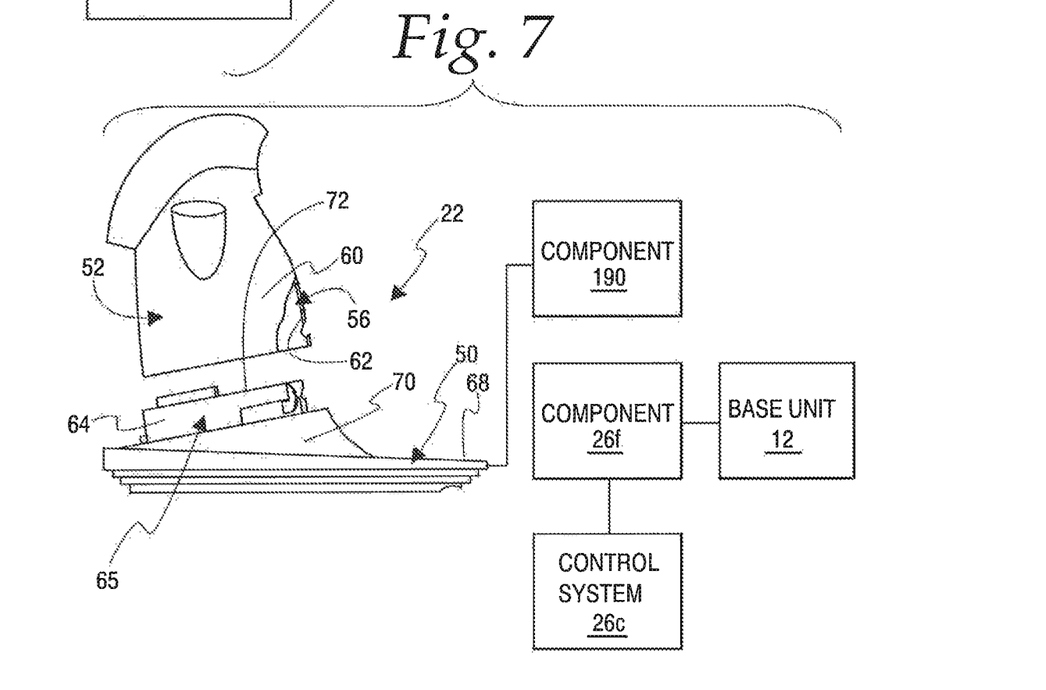
FIG. 7 is an enlarged, exploded, side elevation view of the second subassembly in FIGS. 4-6.
Figure 8:
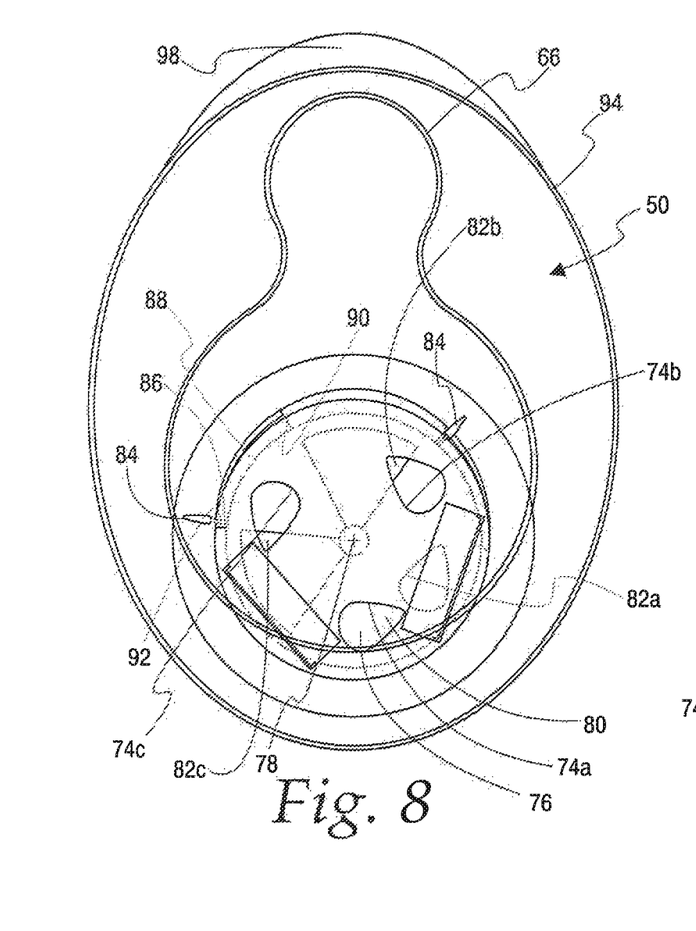
FIG. 8 is an enlarged, bottom view of the second subassembly in FIGS. 4-7 and showing a control plate in a first position to provide for first vapor flow characteristics.

As shown in FIG. 7, the second subassembly 22 may incorporate a component 190 that cooperates with a component 26f on the base unit 12 to cause the control system 26c to turn the apparatus 10 off as the second subassembly 22 is separated from the base unit 12.

An optional fitting 194 may be provided to nest against the surface 148 and has an upwardly opening receptacle 196 for a supply of fluid that produces a desired aroma when heated by the rising vapor.

Figure 16:
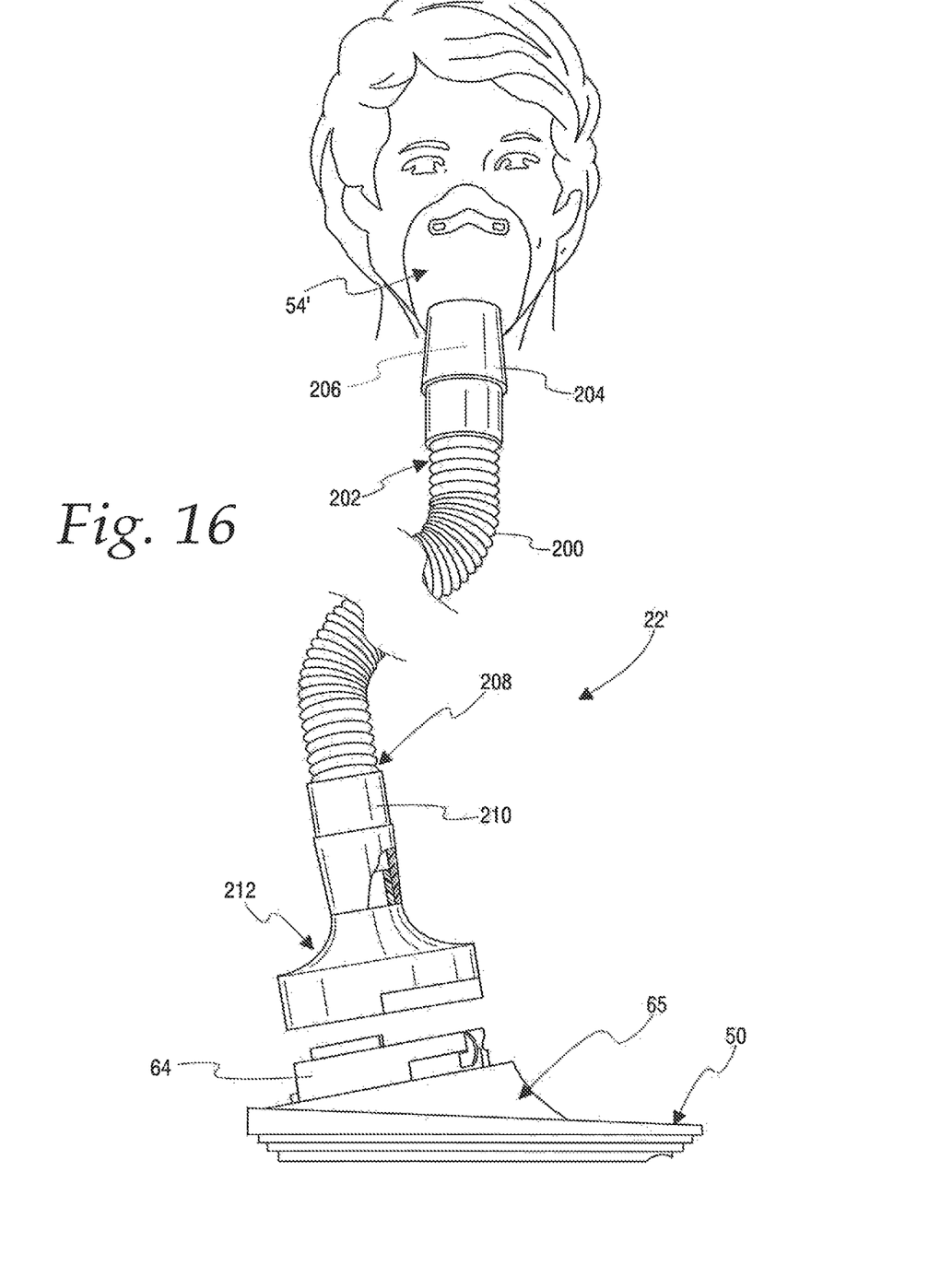
FIG. 16 is an exploded, side elevation view of a modified form of the second subassembly.

In FIG. 16, a modified form of the second subassembly is shown at 22' that utilizes the aforementioned adaptor 50 with the cap 65 having the rim 64. In place of the mask housing 54, a mask housing 54' is utilized. The mask housing 54' is placed in fluid communication with the receptacle 34 on the base unit 12 through a flexible, insulated tube 200. The tube 200 has a first end 202 with a fitting 204 thereon that attaches to a complementary fitting 206 on the mask housing 54'. The opposite tube end 208 has a fitting 210 attached to an adaptor 212. The adaptor 212 is configured to be slid over and frictionally surround the rim 64 to maintain the adaptor 212 on the adaptor 50.

With this arrangement, a user may have more freedom to use the inhaling function while being away from the base unit 12 a distance as dictated by the length of the flexible tube 200.

The foregoing disclosure of specific embodiments is intended to be illustrative of the broad concepts comprehended by the invention.

The invention claimed is:

1. A vapor delivery system comprising:
  a base unit comprising a vapor generator so that the base unit is configured to generate a supply of vapor; and
  a vapor control system usable ire conjunction with the base unit and configured to allow a user to selectively:
  a) cause vapor generated by the base unit to be discharged primarily to a surrounding space within which the base unit resides to thereby increase vapor density in the surrounding space; and b) cause vapor generated by the base unit to be discharged primarily to a vapor guide structure configured to: i) be placed operatively with respect to a user's face; and ii) guide discharging vapor generated by the base unit into at least one of the user's nose and mouth with the vapor guide structure placed operatively with respect to the user's face,
  wherein the vapor delivery system has first and second different states, with the vapor delivery system in the first state vapor generated by the base unit is discharged primarily to the surrounding space, and with the vapor delivery system in the second state vapor generated by the base unit is discharged primarily to the vapor guide structure,
  wherein the vapor control system comprises a first subassembly and a second subassembly, the first and second subassemblies interchangeably operatively connected to the base unit, one in place of the other, to respect very place the delivery system in the first and second states,
  wherein with the first subassembly operatively connected to the base unit, the first subassembly is configured to cause vapor generated by the base unit to be guided in a first manner into the surrounding space and wherein the first subassembly comprises a housing defining a reservoir for a supply of liquid to be delivered to the base unit.

2. The vapor delivery system according to claim 1 wherein the vapor guide structure comprises a mask housing that is configured to: a) conform at least nominally to the user's face with the vapor guide structure placed operatively with respect to the user's face; and b) define a chamber over the at least one of the user's nose and mouth configured to guide discharged vapor generated by the base unit into the at least one of the user's nose and mouth with the vapor guide structure placed operatively with respect to the user's face.

3. The vapor delivery system according to claim 1 wherein the base unit comprises a receptacle for a supply of liquid to be vaporized by the vapor delivery system.

4. The vapor delivery system according to claim 3 wherein the first subassembly comprises a housing defining a reservoir for a supply of liquid, the reservoir in fluid communication with the receptacle with the vapor delivery system in the first state.

5. The vapor delivery system according to claim 2 wherein the base unit comprises a receptacle for a supply of liquid to be vaporized by the vapor delivery system and the receptacle is in fluid communication with the chamber with the vapor delivery system in the second state.

6. The vapor delivery system according to claim 5 wherein the second subassembly is configured to allow a user to selectively control a rate of vapor delivery from the base unit to the mask housing chamber.

7. The vapor delivery system according to claim 6 wherein the mask housing has at least one vent opening through which fluid can discharge from the mask housing chamber to the surrounding space with the vapor guide structure placed operatively with respect to the user's face.

8. The vapor delivery system according to claim 7 wherein the second subassembly comprises an adaptor that is configured to be supported on the base unit with the vapor delivery system in the second state and the second subassembly further comprises a first unit that is releasably connected to the adaptor and defines the mask housing.

9. The vapor delivery system according to claim 8 wherein the first unit is made from a formed flexible material.

10. The vapor delivery system according to claim 4 wherein the first subassembly comprises an adaptor that is configured to be supported on the base unit with the vapor delivery system in the first state.

11. The vapor delivery system according to claim 10 wherein the adaptor is configured to be separated from the housing.

12. The vapor delivery system according to claim 10 wherein the adaptor defines an upwardly converging surface around a vapor passage/space that guides upward vapor flow from the base unit.

13. The vapor delivery system according to claim 8 wherein the adaptor is configured to vertically overlie a portion of the receptacle.

14. A vapor delivery system comprising:
  a base unit configured to generate a supply of vapor; and
  a vapor control system configured to allow a user to selectively: a) cause vapor generated by the base unit to be discharged primarily to a surrounding space within which the base unit resides to thereby increase vapor density in the surrounding space with the vapor delivery system in a first state; and b) cause vapor generated by the base unit to be discharged primarily to a vapor guide structure configured to: i) be placed operatively with respect to a user's face; and ii) guide discharging vapor generated by the base unit into at least one of the user's nose and mouth with the vapor guide structure placed operatively with respect to the user's face with the vapor delivery system in a second state,
  wherein the base unit comprises a receptacle for a supply of liquid to be vaporized by the vapor delivery system,
  wherein the vapor control system comprises a first subassembly comprising a housing defining a reservoir for a supply of liquid, the reservoir in fluid communication with the receptacle with the vapor delivery system in the first state,
  wherein the first subassembly comprises an adaptor that is configured to be supported on the base unit with the vapor delivery system in the first state, wherein the adaptor defines an upwardly converging surface around a vapor passage/space that guides upward vapor flow from the base unit, wherein the reservoir has a vertical depth and the upwardly converging surface extends over at least a part of the vertical depth of the reservoir.

15. The vapor delivery system according to claim 14 wherein the housing defines a downwardly converging collection surface that is configured to funnel liquid downwardly into the vapor passage.

16. The vapor delivery system according to claim 15 wherein the downwardly converging collection surface extends over at least a part of the vertical depth of the reservoir.

17. A vapor delivery system comprising:
a base unit comprising a receptacle for a supply of liquid and configured to generate a supply of vapor from liquid in the receptacle; and
a vapor control system configured to allow a user to selectively: a) cause vapor generated by the base unit to be discharged primarily to a surrounding space within which the base unit resides to thereby increase vapor density in the surrounding space with the vapor delivery system in the first state; and b) cause vapor generated by the base unit to discharged primarily to a vapor guide structure configured to: i) be placed operatively with respect to a user's face, and ii) guide discharging generated by the base unit into at least one of the user nose and mouth with the vapor guide structure placed operatively with respect to the user's face with the vapor delivery system in a second state, wherein a first subassembly of the vapor control system comprises a housing defining a reservoir or a supply of liquid, the reservoir in fluid communication with the receptacle with the fluid delivery system in the first state, wherein the first subassembly comprises an adaptor that is configured to be supported on the base unit with the vapor delivery system in the first state, wherein the adaptor is configured to be separated from the housing, wherein the base unit and adaptor are configured to cause environmental air and vapor generated by the base unit to be mixed in a space bounded by a surface on the adaptor.

* * * * *

UNITED STATES PATENT AND TRADEMARK OFFICE
CERTIFICATE OF CORRECTION

PATENT NO. : 10,729,871 B2
APPLICATION NO. : 15/271927
DATED : August 4, 2020
INVENTOR(S) : Dirk Niedermann et al.

It is certified that error appears in the above-identified patent and that said Letters Patent is hereby corrected as shown below:

In the Claims

Claim 1 should read:
1. A vapor delivery system comprising:
a base unit comprising a vapor generator so that the base unit is configured to generate a supply of vapor; and
a vapor control system usable in conjunction with the base unit and configured to allow a user to selectively: a) cause vapor generated by the base unit to be discharged primarily to a surrounding space within which the base unit resides to thereby increase vapor density in the surrounding space; and b) cause vapor generated by the base unit to be discharged primarily to a vapor guide structure configured to: i) be placed operatively with respect to a user's face; and ii) guide discharging vapor generated by the base unit into at least one of the user's nose and mouth with the vapor guide structure placed operatively with respect to the user's face,
wherein the vapor delivery system has first and second different states, with the vapor delivery system in the first state vapor generated by the base unit is discharged primarily to the surrounding space, and with the vapor delivery system in the second state vapor generated by the base unit is discharged primarily to the vapor guide structure,
wherein the vapor control system comprises a first subassembly and a second subassembly, the first and second subassemblies interchangeably operatively connected to the base unit, one in place of the other, to respectively place the delivery system in the first and second states,
wherein with the first subassembly operatively connected to the base unit, the first subassembly is configured to cause vapor generated by the base unit to be guided in a first manner into the surrounding space and wherein the first subassembly comprises a housing defining a reservoir for a supply of liquid to be delivered to the base unit.

Claim 17 should read:
17. A vapor delivery system comprising:
a base unit comprising a receptacle for a supply of liquid and configured to generate a supply of vapor from liquid in the receptacle; and Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office* a vapor control system configured to allow a user to selectively: a) cause vapor generated by the base unit to be discharged primarily to a surrounding space within which the base unit resides to thereby increase vapor density in the surrounding space with the vapor delivery system in the first state; and b) cause vapor generated by the base unit to be discharged primarily to a vapor guide structure configured to: i) be placed operatively with respect to a user's face; and ii) guide discharging vapor generated by the base unit into at least one of the user's nose and mouth with the vapor guide structure placed operatively with respect to the user's face with the vapor delivery system in a second state, wherein a first subassembly of the vapor control system comprises a housing defining a reservoir for a supply of liquid, the reservoir in fluid communication with the receptacle with the fluid delivery system in the first state, wherein the first subassembly comprises an adaptor that is configured to be supported on the base unit with the vapor delivery system in the first state, wherein the adaptor is configured to be separated from the housing, wherein the base unit and adaptor are configured to cause environmental air and vapor generated by the base unit to be mixed in a space bounded by a surface on the adaptor.